(12) United States Patent
Anaokar et al.

(10) Patent No.: US 7,214,504 B2
(45) Date of Patent: May 8, 2007

(54) TEST STRIP FOR DETERMINING CONCENTRATION OF TRIGLYCERIDES

(75) Inventors: Sunil G. Anaokar, Indianapolis, IN (US); Gena Lynn Antonopoulos, Indianapolis, IN (US); Patrick Cunningham, Indianapolis, IN (US)

(73) Assignee: Polymer Technology Systems, Inc., Indianapolis, IN (US)

( * ) Notice: Subject to any disclaimer, the term of this patent is extended or adjusted under 35 U.S.C. 154(b) by 494 days.

(21) Appl. No.: 10/334,044

(22) Filed: Dec. 30, 2002

(65) Prior Publication Data

US 2003/0170768 A1 Sep. 11, 2003

Related U.S. Application Data

(60) Provisional application No. 60/344,300, filed on Dec. 28, 2001.

(51) Int. Cl.
*C12Q 1/34* (2006.01)
(52) U.S. Cl. .......................... 435/18; 422/56
(58) Field of Classification Search .............. 435/19, 435/4, 975, 18; 422/56
See application file for complete search history.

(56) References Cited

U.S. PATENT DOCUMENTS

| | | | | |
|---|---|---|---|---|
| 5,126,246 A | * | 6/1992 | Imamura et al. | 435/19 |
| 5,156,954 A | * | 10/1992 | Mielke et al. | 435/18 |
| 5,597,532 A | * | 1/1997 | Connolly | 422/58 |
| 2003/0170768 A1 | * | 9/2003 | Anaokar et al. | 435/19 |

OTHER PUBLICATIONS

PTS PANELS Triglycerides Test Strips Instructions, (PS-001596 Rev. 2 May 2002).*

Cholestech LDX®, Lipid Profile plus Glucose-II, Total Cholesterol, HDL Cholesterol, Triglycerides and Glucose Panel, ackage insert.

LIPID Profile plus Glucose, Cholestech LDX®, Lipid Profile plus Glucose-II, Total Cholesterol, HDL Cholesterol, Triglycerides and Glucose Panel, Box Label.

LIPID Profile plus Glucose, Cholestech LDX®, Lipid Profile plus Glucose-II, Total Cholesterol, HDL Cholesterol, Triglycerides and Glucose Panel, cassette label, ® 1999.

Cholestech LDX®, Lipid Profile plus Glucose-II, Total Cholesterol, HDL Cholesterol, Triglycerides and Glucose Panel, ackage insert, no date given.

LIPID Profile plus Glucose, Cholestech LDX®, Lipid Profile plus Glucose-II, Total Cholesterol, HDL Cholesterol, Triglycerides and Glucose Panel, Box Label, no date given.

LIPID Profile plus Glucose, Cholestech LDX®, Lipid Profile plus Glucose-II, Total Cholesterol, HDL Cholesterol, Triglycerides and Glucose Panel, cassette label,® 1999.

* cited by examiner

*Primary Examiner*—Ralph Gitomer
(74) *Attorney, Agent, or Firm*—Patton Boggs LLP (57) ABSTRACT

A dry-phase triglycerides test strip that can be stored at room or elevated temperatures for several months without significant degradation in its effectiveness. The test strip includes a test membrane which receives plasma and forms a colored response in proportion to concentration of triglycerides in the plasma. The test membrane is impregnated with an aqueous solution containing lipoprotein lipase (LPL) and 4-aminoantipyrine (4AAP). The inventors have found that by reducing the pH of the impregnating solution to less than that of the recommended pH range for one of the key components (viz., less than pH 6.0), overall stability of the test strips was dramatically improved. The improvement in storage capability of these triglycerides test strips represents not just a difference in degree, but a difference in kind.

6 Claims, 6 Drawing Sheets

FIG. 2 -- PRIOR ART FORMULATION of TRIG TEST MEMBRANE CONCENTRATION OF TRIGS: 403 - 491 mg/dL

FIG. 4

FIG. 5 CONCENTRATION OF TRIGS: 200 - 269 mg/dL

FIG. 6 CONCENTRATION OF TRIGS: 403 – 491 mg/dL

TEST STRIP FOR DETERMINING CONCENTRATION OF TRIGLYCERIDES

RELATED APPLICATIONS

This application claims priority to U.S. Provisional Patent Application Ser. No. 60/344,300, filed Dec. 28, 2001. This application incorporates by reference herein in its entirety another application entitled Test Strip for Determining Concentration of Multiple Analytes, which is commonly owned with the present application and has been filed on even date herewith.

FIELD OF THE INVENTION

The present invention relates generally to testing of body fluids for concentration of analytes and more particularly to methods and apparatus for dry-phase testing of analytes.

BACKGROUND

The level of certain analytes in blood and other body fluids can predict disease or risk thereof. For example, the amounts of cholesterol and triglycerides in blood are a significant indicator of risk of coronary heart disease ("CHD"). Excess triglycerides in plasma is called "hypertriglyceridemia," and is linked to the occurrence of atherosclerosis and CHD in some people. Elevated triglycerides may be a consequence of other disease, such as untreated diabetes mellitus. Like cholesterol, increases in triglyceride levels can be detected by plasma measurements.

A number of enzymatic methods have been developed for determining triglycerides in plasma or serum. One method involves the following reaction pathway.

Dry-phase test strips are known which rely upon the above reaction pathway and which include the reagents necessary for reaction loaded into their reaction or test membranes. In these test strips, blood cells are separated from plasma, and the resulting plasma is then passed into one or more test membranes. Color is produced in the test membrane and is read by reflectance photometry and correlated to concentration of triglycerides. In a dry-phase test system, all of the reagents to carry out the color producing reaction are typically loaded into a single test membrane. Thus, the pH of the aqueous solution used to load the reagents in the test membrane must be compatible with all reagents.

In the above pathway, the reagents 4-aminoantipyrine (4AAP) and lipoprotein lipase (LPL) are critical. Commercially available LPL is typically derived from pseudomonas. LPL starts the reaction above by hydrolyzing the triglycerides into their component fatty acid and glycerol molecules as shown above. LPL typically requires a pH range of 6–9 for its activity. On the other hand, the Trinder reagent 4AAP, which is responsible for color formation as shown in the last step of the above pathway, is not stable in alkaline environments. Generally speaking, the lower the pH, the more stable is 4AAP. Thus, there is a delicate balance of maintaining the pH of the impregnating solution high enough to maintain the activity of LPL on the one hand, and maintaining the pH low enough to maintain the stability of the 4AAP on the other hand. Stability of triglyceride strips is a problem, and the best commercially available triglycerides test strips known to applicants require storage at 4° C. to maintain their stability for even a couple of months. In these prior art test strips, the test membrane is impregnated with a solution whose pH is maintained at pH 6.2–6.7. Further, an aqueous Klucel Citrate foundation is mixed separately and added to the impregnating solution, and the foundation's pH is also maintained at pH 6.2–6.7.

Figure 1:
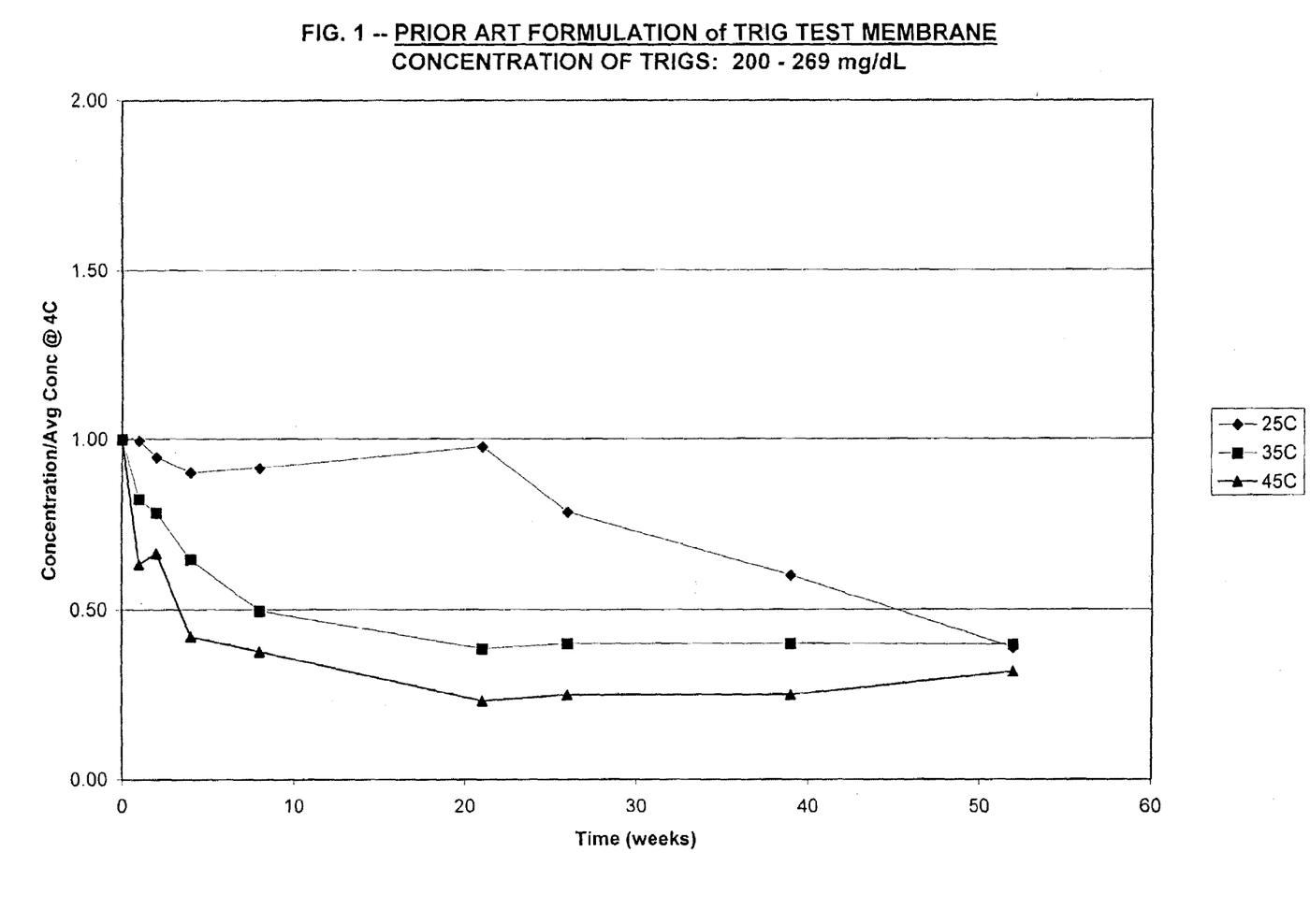
FIG. 1 is a graph representing the ratio of measured concentration of triglycerides from prior art strips stored at an elevated temperature to measured concentration of prior art triglycerides from strips stored at 4° C.
Figure 2:
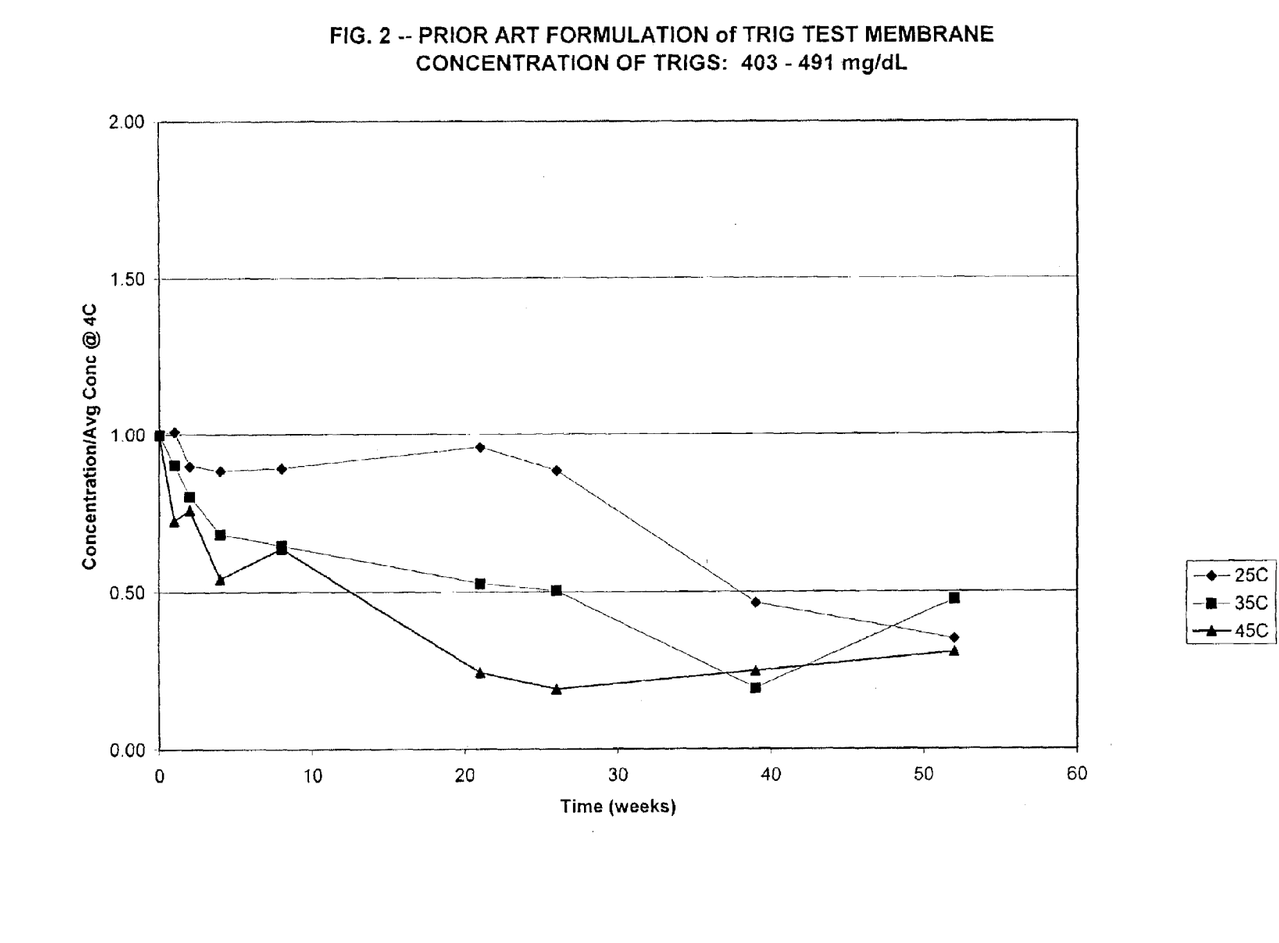
FIG. 2 is a graph like that described with reference to FIG. 4, except the test sample contained a higher concentration of triglycerides.

Prior art FIGS. 1 and 2 illustrate that, prior art triglycerides test strips made by the assignee of the present invention are not stable for a significant length of time above room temperature. To generate the graphs shown in FIGS. 1 and 2, a control set of prior art test strips was stored at 4° C., whereas other prior art test strips were stored at 25° C., 35° C. and 45° C., respectively. Triglycerides concentration in whole blood samples was measured at various time intervals using the refrigerated strips as a control and the other strips stored at elevated temperatures. The ratio of the concentration of triglycerides measured from strips stored at 4° C. versus the strips stored at 25° C., 35° C. and 45° C. are plotted in FIGS. 1 and 2. FIG. 2 includes samples known to have a higher concentration of triglycerides than the samples plotted in FIG. 1. As can be appreciated, serious degradation in test result occurs within 4 weeks of storage for the strips stored at 35° C. and 45° C. For the strips stored at 25° C., the results are stable for a longer duration, but begin to degrade after 20 weeks of storage as shown.

It can be appreciated that test strips may spend several weeks in storage at the manufacturer's facility before they are transported. During transportation, if the strips are shipped without being refrigerated, the temperatures to which they are exposed can be quite high, up to 45° C. As can be appreciated, prior art triglycerides test strips cannot withstand such high temperatures during transportation. Thus, it would be desirable to enhance the stability of triglyceride test strips at room temperatures and elevated temperatures such that they can be shipped with other non-refrigerated items and stored in a room temperature environment.

SUMMARY OF THE INVENTION

The present invention provides a dry-phase triglycerides test strip that can be stored at room or elevated temperatures for several months without significant degradation in its effectiveness. Amazingly and quite surprisingly, the inventors of the present invention found that by reducing the pH of the aqueous solution used to impregnate the test layer to less than that of the recommended optimum range for one of the key components, overall stability of the test strips is dramatically improved. The improvement obtained thereby represents not just a difference in degree, but a difference in kind.

In one form thereof, the present invention provides a test strip for measuring concentration of triglycerides in a whole blood sample. The test strip includes a test membrane which receives plasma and forms a colored response in proportion to concentration of triglycerides in the plasma. The test membrane is impregnated with an aqueous solution containing lipoprotein lipase (LPL) and 4-aminoantipyrine (4AAP). The pH of the aqueous solution is less than 6.0, whereby the test strip is stable at room temperature for several months.

In a preferred form thereof, the pH of the impregnating solution is about 5.9. In a further preferred form, the test strip also includes a disbursement layer and a blood separation layer adjacent to and in fluid communication with the disbursement layer and the test membrane. Optionally, a blank layer may be disposed between the blood separation layer and the test membrane. The blank layer traps remaining blood cells that may not be retained by the blood separation layer.

The advantages of not having to refrigerate the triglyceride test strips of the present invention are significant. The flexibility in marketing, displaying and packaging the strips in stores and pharmacies is increased exponentially. Refrigerated items often cannot be displayed on store shelves, and the consumer may not realize that he or she has to inquire about their availability. With the present invention, the triglyceride strips may be displayed on the same shelf on which, for example, glucose meters, blood pressure instruments and other non-perishable test strips such as glucose strips are displayed. Since the strips need not be refrigerated, they may be packaged and sold along with the test instrument which reads them, or other test strips that need not be refrigerated. Of course, the advantages to the user in not having to refrigerate the strips are also significant.

BRIEF DESCRIPTION OF THE DRAWINGS

The above-mentioned and other advantages of the present invention, and the manner of obtaining them, will become more apparent and the invention itself will be better understood by reference to the following description of the embodiments of the invention taken in conjunction with the accompanying drawings, wherein.

Corresponding reference characters indicate corresponding parts throughout the several views.

DETAILED DESCRIPTION

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

Figure 3:
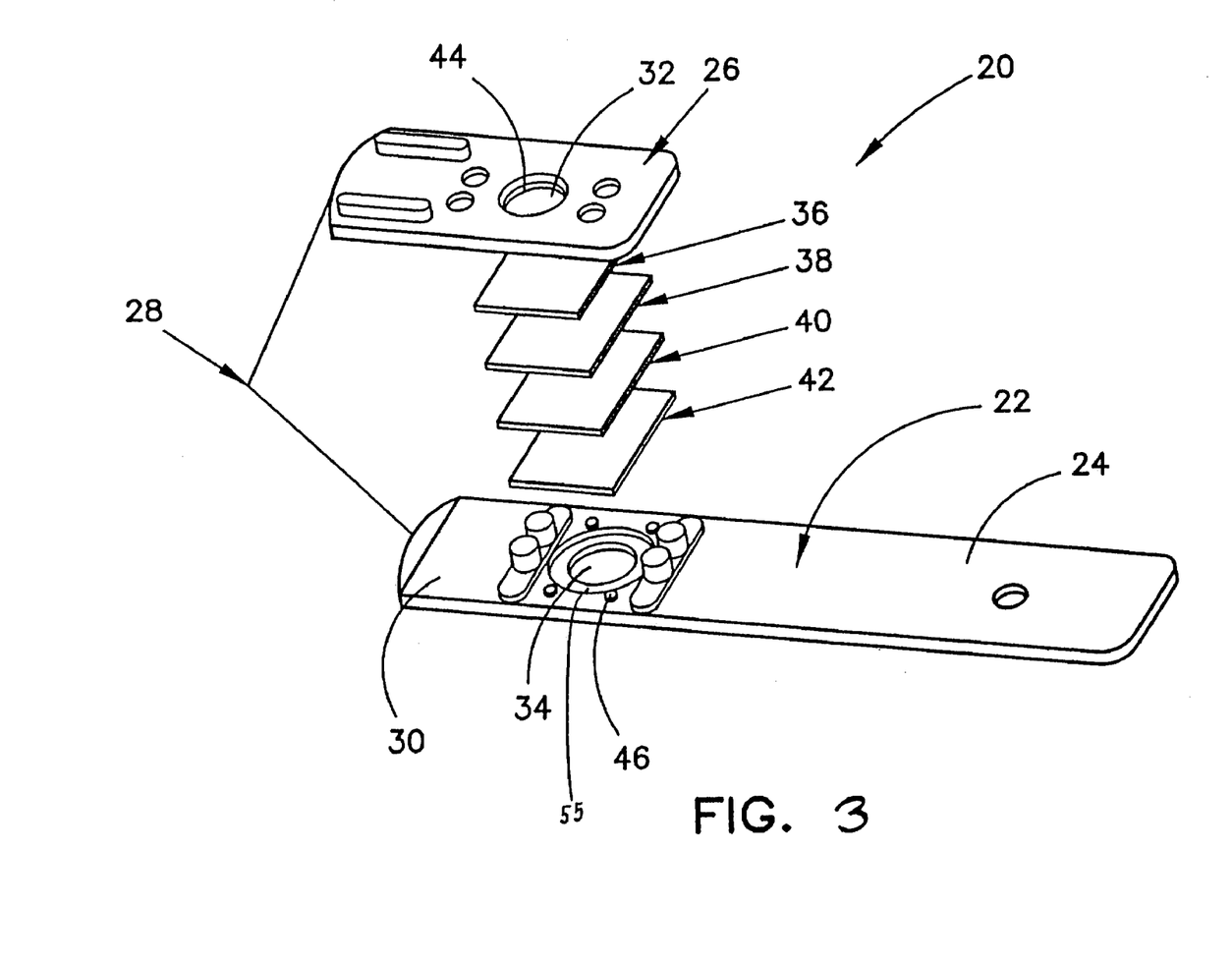
FIG. 3 is an exploded perspective view of a test strip in accordance with the present invention.

Referring now to FIG. 3, test strip 20 includes test strip holder 22 which is preferably formed by injection molding. Test strip holder includes handle 24 and end portion 26 which is preferably hingedly attached by hinge portion 28 to second end portion 30, shown exploded away in FIG. 3. Portion 26 is foldable about hinge portion 28 over portion 30 as shown. End portion 26 includes an opening 32 while end portion 30 includes a complementary spaced opening 34. When end portion 26 is folded over end portion 30, openings 32 and 34 are aligned. In its folded position, opening 32 in holder 22 defines an application window for depositing a body fluid sample while opening 34 defines a test reading window in which optoelectronic measurements of chemistry test reactions are conducted.

A test strip holder essentially the same as that described with reference to FIG. 1 is shown and described in U.S. Pat. No. 5,597,532, the disclosure of which is hereby incorporated by reference. The test strip holder is not critical to the invention and other suitable embodiments of a test strip holder are contemplated by this invention. The particular test strip described herein is suitable for use with an optoelectronic instrument sold under the trademark Cardio Chek, commercially available from Polymer Technology Systems, Inc., Indianapolis, Ind.

Figure 4:
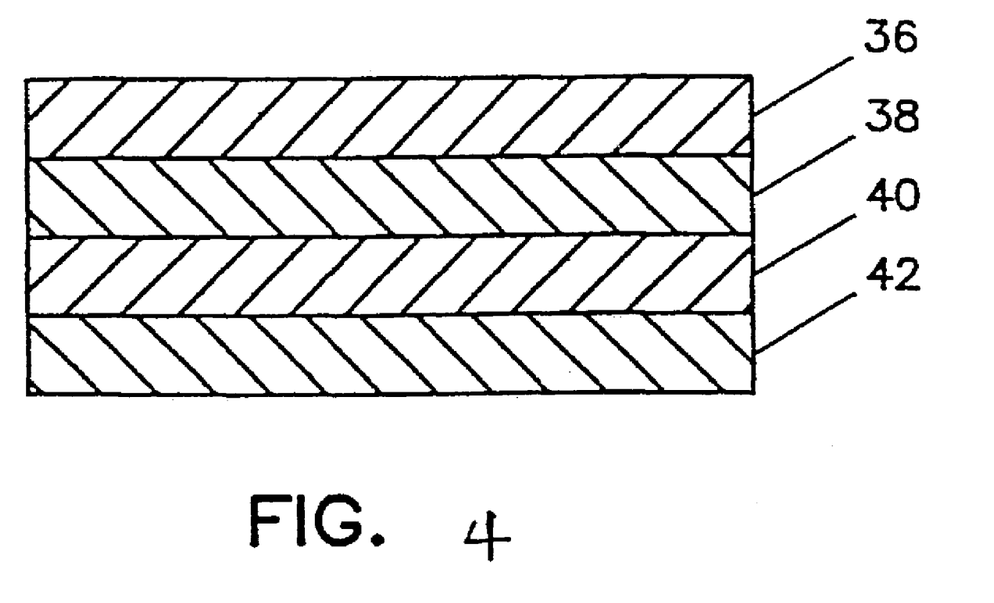
FIG. 4 is a cross sectional view of the layers which comprise the test strip of FIG. 1.

Turning now to FIG. 3 and FIG. 4, there are four layers held within test strip holder 22 without requiring adhesives. It has been found that it is desirable to exert a compressive force upon the layers between end portion 26 and end portion 30. The proper compressive force exerted upon the layers is a design variable that can be adjusted by (1) adjusting the available space between ends 26 and 30 when the strip is snapped together; (2) adjusting the size and length of rim 44, which rim depends downwardly from opening 32 and engages the top layer held between ends 26 and 30; (3) adjusting the size of protuberances 46, which also engage the layers; and (4) adjusting the depth of shelf 55. A desirable compressive force to be exerted on the test layers by the test strip reduces the height of the stack of layers by about twenty percent (20%) from the height the layers would occupy if no compressive force were exerted. It is believed that compressing the layers removes air pockets within the test matrix and thereby improves the speed with which the physical and chemical processes take place. This, in turn, improves the precision of the test. Compression is effectuated by sandwiching the stack of layers between downwardly depending rim or boss 44 and shelf 55.

The top layer 36 is a disbursement or spreader mesh layer formed of, for example, woven materials such as polyester or cotton, non-woven fabric, gauze or monofilament yarn. One suitable material for spreader layer 36 is a Sefar PeCap (07-17/9) available from Sefar American, Inc., DePew, N.Y.

Layer 36 provides rapid and even disbursement of a body fluid such as whole blood or plasma. It has been found that test strip 20 works without layer 36, but layer 36 is desirable because it provides a more uniform distribution of blood to the subjacent layer and the test results vary less when the spreader layer is used.

Beneath and in fluid communication with disbursement or spreader layer 36 is layer 38. Layer 38 separates red blood cells from whole blood and passes a fluid containing a remaining portion of blood cells therethrough. It has been experimentally found that about 80%–90% of red blood cells are retained within layer 38 during the duration of the test period. Layer 38 is generally a glass fiber matrix. A suitable commercial material for layer 38 is Ahlstrom Grade 144, thickness 0.378 mm, available from Ahlstrom Filtration, Inc., Mt. Holly Springs, Pa. Other glass fiber matrices could be substituted. Generally, layer 38 should include glass fibers with a diameter of 0.5 to 2 microns and a density of 0.1 to 0.5 g/cm$^3$.

Beneath and in fluid communication with layer 38 is layer 40. Layer 40 is also preferably a randomly dispersed glass fiber matrix. In the illustrated embodiment, layer 40 includes a blend of glass microfiber, cellulose fiber, and synthetic staple fiber. The glass microfiber component consists of alkali-containing or alkali-free borosilicate glass or pure quartz fibers, having a mean fiber diameter of 0.3 to 0.7 micrometers. The bulk density of the glass microfiber component is less than 0.1 g/cm$^3$, and is typically about 0.05 g/cm$^3$. One suitable membrane for layer 40 is CytoSep® grade 1660 membrane, 12.9 mils thick, available from Pall Specialty Materials, Port Washington, N.Y. Another suitable membrane for layer 40 is paper grade 595, 0.180 mm (7.1 mil) thick, available from Schleicher & Schuell, Keene, N.H. Layer 40 retains the remainder of red blood cells that escape from layer 38, such that layer 40 provides clean plasma to layer 42. Layer 40 is untreated, and is referred to herein as a "blank" layer.

Figure 5:
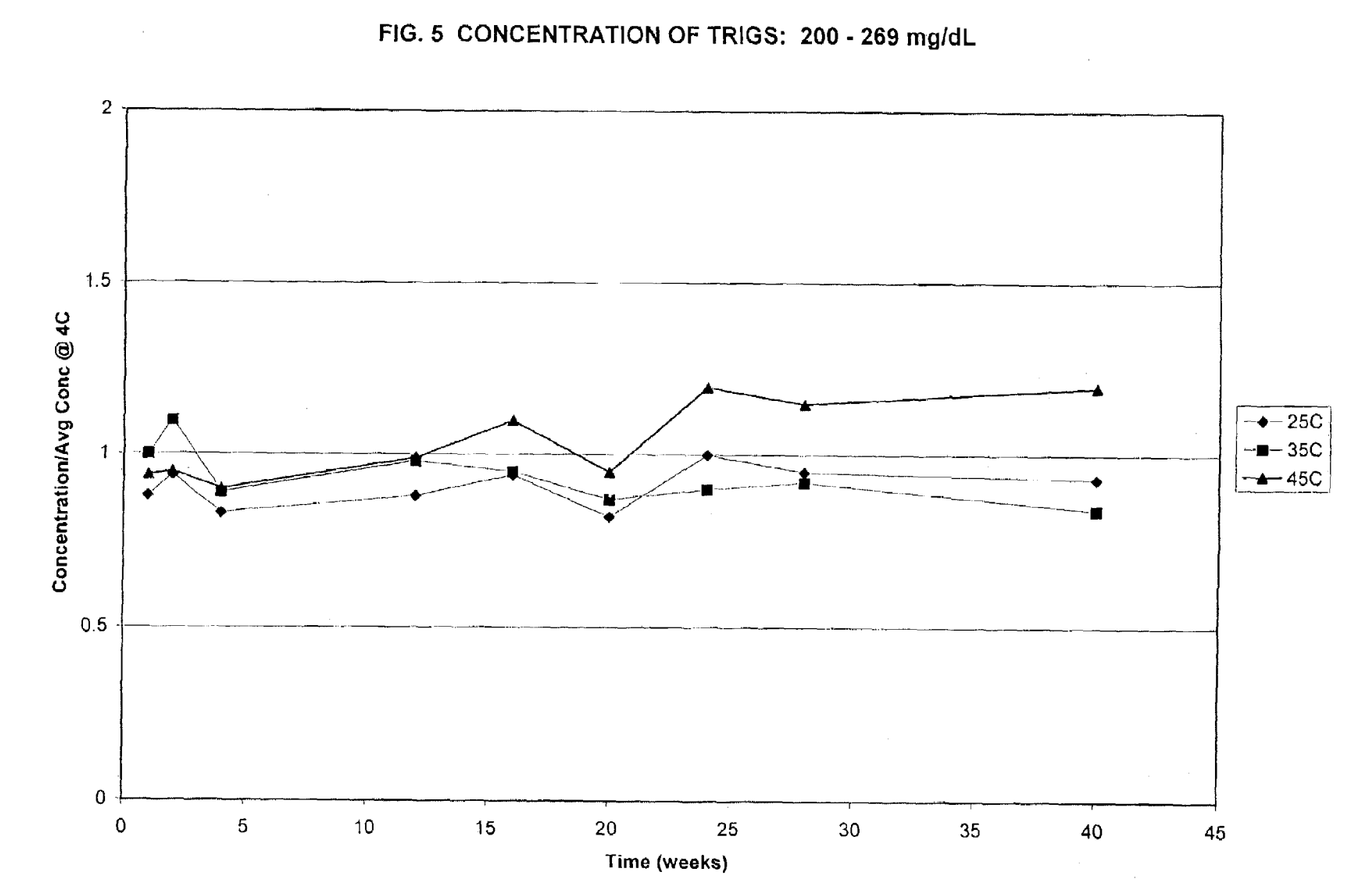
FIG. 5 is a graph representing the ratio of measured concentration of triglycerides from strips stored at an elevated temperature to measured concentration of triglycerides from strips stored at 4° C.
Figure 6:
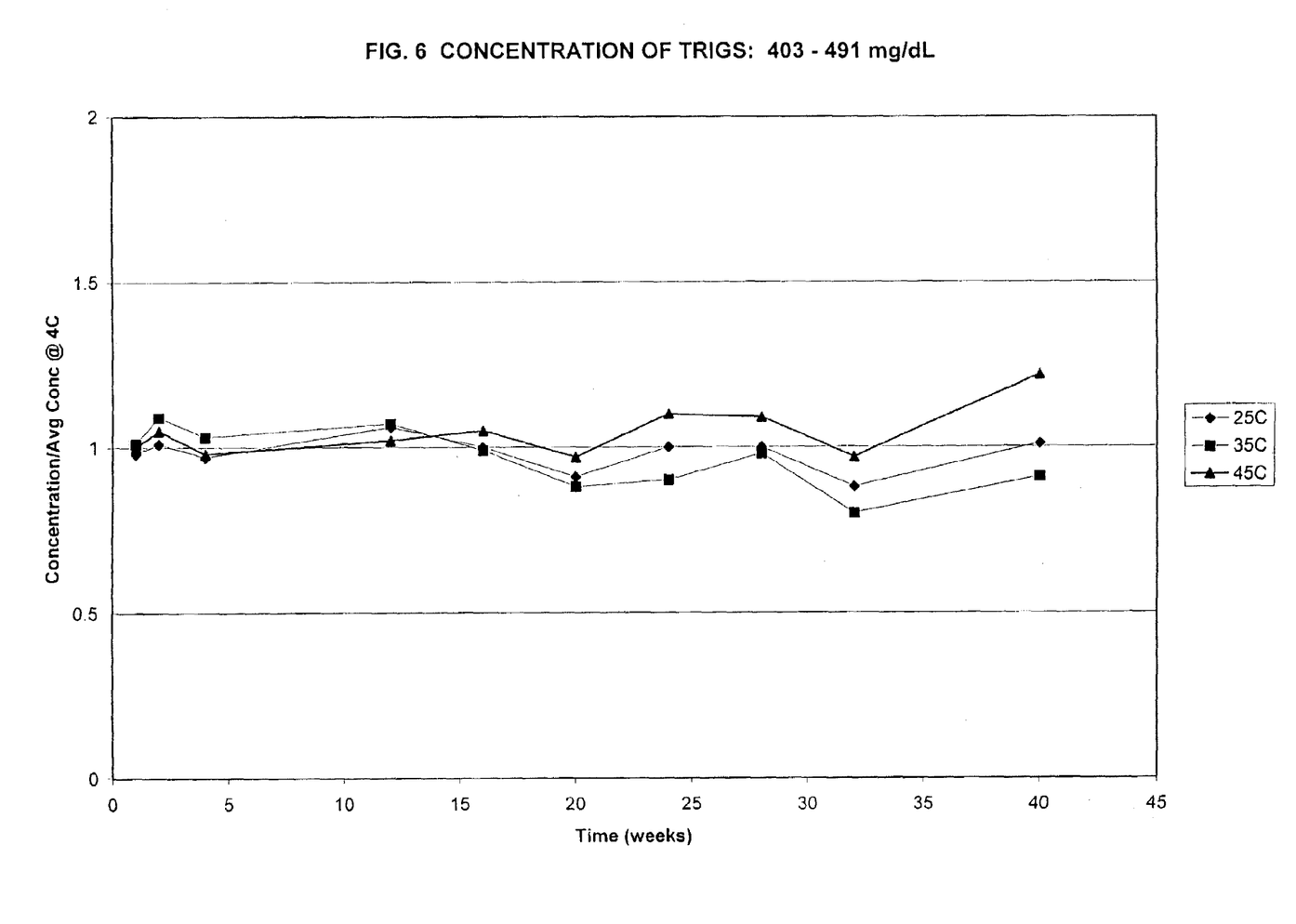
FIG. 6 is a graph like that described with reference to FIG. 4, except the test sample contained a higher concentration of triglycerides.

Below, adjacent to and in fluid communication with layer 40 is test membrane 42 where the reagents for the reaction are impregnated. Surprisingly, as alluded to above, it has been found that by maintaining the pH of the impregnating solution below 6.0, more preferably about 5.9, the stability of the triglyceride test strips is greatly improved, to the extent that they can be stored at room and elevated temperatures for several months, as indicated in FIGS. 5 and 6. Hitherto, all known triglyceride test strips, including applicants,' had to be stored at 4° C. Indeed, the inventors' design goal was to modify the pH of the impregnating solution to merely improve the stability of the strips in a refrigerated environment.

Quite remarkably and surprisingly, however, the inventors found that by reducing the pH of the impregnating solution to less than that of the recommended optimum range for LPL, stability was dramatically improved—to the extent that refrigerated storage was no longer necessary. The results obtained by changing the pH represent not just a difference in degree, but a difference in kind. For example, when formed with an aqueous impregnating solution of pH 6.2–6.7, which is only marginally higher than the inventive pH, the test strips are stable when refrigerated at 4° C., but cannot be used if not refrigerated because the LPL loses its enzymatic activity and, consequently, test results become inaccurate. (See prior art FIGS. 1 and 2.)

Applicants merely hoped for increased storage duration and stability under refrigeration temperatures. Quite unexpectedly, they found that reducing the pH resulted in a test strip for which refrigeration is no longer necessary. Further, the manufacturer's suggested pH range for LPL is listed as 6.0–9.0. It was also quite unexpected that the LPL would still work very well at a pH which is outside of its recommended range.

The following examples will allow one of ordinary skill in the art to practice the present invention.

EXAMPLE 1

Preparation of Blood Separation Membrane 38

Ahlstrom Grade 144, which is a glass fiber membrane with a thickness of 0.378 mm, was impregnated with a solution with the following composition:

| | |
|---|---|
| D.I. Water | 800 g |
| NaCl | 10 g |
| Sorbitol | 50 g |
| Citric Acid | 0.21 g |
| pH 4.2–4.4 | |
| Q.S. to 1000 mL with D.I. Water | |

The membrane was submersed in a re-circulating bath of impregnation solution at a rate of 0.5 ft/min. It then entered a tunnel of blowing warm air (98°–106° F.) and low humidity (<5% RH) to dry completely.

EXAMPLE 2

Triglyceride Membrane 42 with Chromogen

| | |
|---|---|
| D.I. Water | 405.2 g |
| Triton X-100 | 1 g |
| CHAPS | 0.7 g |
| Klucel Citrate Foundation** | 575.2 g |
| 10% Gantrez AN139 | 20.8 g |
| Calcium Chloride, Anhydrous | 0.2 g |
| Sucrose | 25.2 g |
| Na$_2$ATP | 32 g |
| Adjust pH to 5.70 +/− 0.10 with HCl or NaOH | |
| MAOS | 6.252 g |
| G3P Oxidase | 250 kU |
| Peroxidase | 750 kU |
| LPL-311 | 625.2 kU |
| Glycerol Kinase | 358.4 kU |
| 4-AAP | 5.552 g |
| Record final pH (usually around 5.9) | |

The membrane was submersed in a re-circulating bath of impregnation solution at a rate of 1 ft/min. It then entered the tunnel of blowing warm air (98°–106° F.) and low humidity (<5% RH) to dry completely.

**Klucel Citrate Foundation

| | |
|---|---|
| D.I. Water | 800 g |
| Sodium Citrate | 20.6 g |
| Citric Acid, monohydrate | 6.3 g |
| Magnesium Chloride | 1.434 g |
| BSA, standard powder | 20 g |
| Sodium Benzoate | 2 g |
| Klucel EXF | 10 g |
| Adjust pH to 5.60 +/− 0.10 with HCl or NaOH | |
| Q.S. to 1000 mL with D.I. Water | |
| Final pH 5.6 +/− 0.10, adjust if necessary | |

EXAMPLE 3

Triglyceride Strip 20 Assembly:

The test layers or membranes 36–42 were placed in the following order between the pins in the test strip holders: Bottom layer 42 or Reagent Impregnated Triglyceride Membrane, then layer 40, which was an untreated CytoSep® Grade 1660 layer, then the Blood Separation Membrane 38 (Ahlstrom Grade 144), and finally the Mesh screen layer (Sefar PeCap (07-17/9)). The test strip holders were folded and pressed to ensure closure. The strip holders were staked using a cold stake press, and then cut to individual strips and placed in vials with desiccant.

EXAMPLE 4

Curing at 4° C., 25° C., 35° C., and 45° C.

Slit reels (0.25 inch) of Reagent Impregnated Triglyceride Membrane were placed in 4° C., 25° C., 35° C. and 45° C. environments and allowed to cure for ten days. Next, strips were made using membranes 36–42 prepared using the impregnation solutions of Examples 1 and 2 and the strips then were assembled according to the procedure set forth in Example 3. A curve was set for each temperature as in Example 5.

EXAMPLE 5

Curve Setting

Fresh EDTA whole blood with various levels of triglyceride were obtained and applied to the test strips. Percent reflectance using a red LED was recorded at the reaction endpoint for each temperature.

TABLE 1

4° C.

| Triglyceride Concentration (mg/dL) | % Reflectance Mean (n = 10) |
|---|---|
| 63 | 55.05 |
| 87 | 52.70 |
| 141 | 45.03 |
| 188 | 39.50 |
| 286 | 32.33 |
| 380 | 31.87 |
| 498 | 26.50 |

Using the data from Table 1, a hyperbolic fit was applied to calculate the following curve set.

TABLE 2

4° C.

| Triglyceride Concentration (mg/dL) | % Reflectance |
|---|---|
| 50 | 56.22 |
| 75 | 52.70 |
| 100 | 49.54 |
| 125 | 46.73 |
| 150 | 44.22 |
| 175 | 41.97 |
| 200 | 39.94 |
| 225 | 38.09 |
| 300 | 33.46 |
| 375 | 29.83 |
| 425 | 27.81 |
| 500 | 25.26 |

TABLE 3

25° C.

| Triglyceride Concentration (mg/dL) | % Reflectance Mean (n = 10) |
|---|---|
| 63 | 57.28 |
| 87 | 52.19 |
| 141 | 44.17 |
| 188 | 38.87 |
| 286 | 33.22 |
| 380 | 31.81 |
| 498 | 27.08 |

Using the data from Table 3, a hyperbolic fit was applied to calculate the following curve set.

TABLE 4

25° C.

| Triglyceride Concentration (mg/dL) | % Reflectance |
|---|---|
| 50 | 61.44 |
| 75 | 54.77 |
| 100 | 49.67 |
| 125 | 46.14 |
| 150 | 43.46 |
| 175 | 41.29 |
| 200 | 39.44 |
| 225 | 37.83 |
| 300 | 33.89 |
| 375 | 30.79 |
| 425 | 29.01 |
| 500 | 26.65 |

TABLE 5

35° C.

| Triglyceride Concentration (mg/dL) | % Reflectance Mean (n = 10) |
|---|---|
| 63 | 58.74 |
| 87 | 55.94 |
| 141 | 47.86 |
| 188 | 43.56 |
| 286 | 35.64 |
| 380 | 34.95 |
| 498 | 29.17 |

Using the data from Table 5, a hyperbolic fit was applied to calculate the following curve set.

TABLE 6

35° C.

| Triglyceride Concentration (mg/dL) | % Reflectance |
|---|---|
| 50 | 59.48 |
| 75 | 56.15 |
| 100 | 53.12 |
| 125 | 50.40 |
| 150 | 47.94 |
| 175 | 45.71 |
| 200 | 43.68 |
| 225 | 41.82 |
| 300 | 37.09 |
| 375 | 33.32 |
| 425 | 31.21 |
| 500 | 28.50 |

Data was also generated for the triglycerides strips stored at 45° C., and a hyperbolic fit was applied to generate a curve set. The data is not specifically shown in tables such as those above, but the results are presented below and in FIGS. 5 and 6.

Stability Study

After the curves were set, vials were stored at their respective temperatures. At each time point shown on FIGS. 5 and 6 fresh EDTA whole blood for two levels of triglycerides were obtained and applied to the test strips. The first level of triglycerides concentration was in the range of 200–269 mg/dL (FIG. 5). The second level of triglycerides concentration was in the range of 403–491 mg/dL (FIG. 6).

Percent reflectance using a red LED was recorded at the reaction endpoint for strips stored at each temperature. The graphs of FIGS. 5 and 6 are plots of concentration measured at the endpoint of the color-producing reaction (i.e., which corresponds to the measured concentration of triglycerides) divided by the concentration measured from the (control) strips, i.e., those stored at 4° C. strips.

As can be seen from FIGS. 5 and 6, the triglycerides strips of the present invention can be stored at room and elevated temperatures of 35° C. and 45° C. This is truly a remarkable and significant improvement to the storage ability of dry phase triglycerides test strips.

While a preferred embodiment incorporating the principles of the present invention has been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A method of providing a test strip for use in measuring the concentration of triglycerides in whole blood, said method comprising: (a) forming an aqueous solution for impregnating a test membrane, the solution containing lipoprotein lipase (LPL) and 4-aminoantipyrine (4AAP) and maintaining the pH of the aqueous solution less than pH 6.0; (b) impregnating the test membrane with the aqueous solution; and (c) assembling the test membrane and at least one other test layer into a test strip adapted to receive a quantity of whole blood.

2. The method of claim 1, further comprising the step of storing the test strip at room temperature or above for at least twenty (20) weeks with the test strip remaining substantially stable.

3. The method of claim 2, further comprising the step of storing the test strip at room temperature or above for at least forty (40) weeks with the test strip remaining substantially stable.

4. The method of claim 2, further comprising, before step (a), the step of forming a citrate foundation and maintaining the pH thereof less than 6.0 and using the citrate foundation as a component of the aqueous solution.

5. The method of claim 4, further comprising maintaining the pH of the citrate solution at about pH 5.6.

6. The method of claim 1, further comprising in step (a) maintaining the final pH of the aqueous solution at about 5.9.

* * * * *